United States Patent
Gibot et al.

(10) Patent No.: US 9,255,136 B2
(45) Date of Patent: Feb. 9, 2016

(54) INHIBITING PEPTIDES DERIVED FROM TREM-LIKE TRANSCRIPT 1 (TLT-1) AND USES THEREOF

(75) Inventors: Sebastien Gibot, Vandoeuvres-les-Nancy (FR); Marc Derive, Vandoeuvres-les-Nancy (FR)

(73) Assignees: Institut National de la Sante et de la Recherche Medicale (INSERM), Paris (FR); Universite de Lorraine, Nancy (FR)

( * ) Notice: Subject to any disclaimer, the term of this patent is extended or adjusted under 35 U.S.C. 154(b) by 0 days.

(21) Appl. No.: 13/639,374

(22) PCT Filed: Apr. 8, 2011

(86) PCT No.: PCT/EP2011/055519
§ 371 (c)(1),
(2), (4) Date: Oct. 4, 2012

(87) PCT Pub. No.: WO2011/124685
PCT Pub. Date: Oct. 13, 2011

(65) Prior Publication Data
US 2013/0029921 A1 Jan. 31, 2013

(30) Foreign Application Priority Data
Apr. 8, 2010 (EP) ..................................... 10305364

(51) Int. Cl.
| | | |
|---|---|---|
| A61K 38/08 | (2006.01) | |
| C12N 15/12 | (2006.01) | |
| C12N 15/63 | (2006.01) | |
| A61K 31/7088 | (2006.01) | |
| A61P 29/00 | (2006.01) | |
| C07K 7/06 | (2006.01) | |
| C07K 7/08 | (2006.01) | |
| A61K 38/10 | (2006.01) | |
| C07K 14/705 | (2006.01) | |
| A61K 38/00 | (2006.01) | |

(52) U.S. Cl.
CPC ........... *C07K 14/70503* (2013.01); *A61K 38/00* (2013.01)

(58) Field of Classification Search
CPC . A61K 38/00; A61K 48/00; C07K 14/70503; C12N 15/00
See application file for complete search history.

(56) References Cited

U.S. PATENT DOCUMENTS

| | | |
|---|---|---|
| 4,861,719 A | 8/1989 | Miller |
| 5,270,163 A | 12/1993 | Gold et al. |
| 5,278,056 A | 1/1994 | Bank et al. |
| 5,475,096 A | 12/1995 | Gold et al. |
| 5,882,877 A | 3/1999 | Gregory et al. |
| 6,013,516 A | 1/2000 | Verma et al. |
| 2004/0180409 A1 | 9/2004 | McVicar |
| 2004/0266674 A1* | 12/2004 | Mills et al. ....................... 514/12 |
| 2007/0128698 A1* | 6/2007 | Talor .............................. 435/69.1 |

FOREIGN PATENT DOCUMENTS

| | | | |
|---|---|---|---|
| WO | 94/19478 | 9/1994 | |
| WO | 95/14785 | 6/1995 | |
| WO | 96/22378 | 7/1996 | |
| WO | 01/89568 A1 | 11/2001 | |
| WO | WO 0189568 A1 * | 11/2001 | ........... A61K 39/395 |
| WO | 2010/132370 A2 | 11/2010 | |

OTHER PUBLICATIONS

A Valance Washington, 2002, Initial characterization of TREM-like transcript (TLT)-1: a putative inhibitory receptor within the TREM cluster, Blood Journal, 100:3822-3824.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Josef Vagner, Peptidomimetic, a synthetic tool of drug discovery, 2008, Curr Opin Chem Biol:12(3):292-296.*
Ngo et al, Computational Complexity, Protein Structure Protection, and the Levinthal Paradox, 1994, pp. 491-494.*
Voet et al, Biochemistry, John Wiley & Sons Inc., 1995, pp. 235-241.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Washington et al., "Trem-like transcript-1 protects against inflammation-associated hemorrhage by facilitating platelet aggregation in mice and humans", Journal of Clinical Investigation, Jun. 2009, pp. 1489-1501, vol. 119, No. 6.
Gattis et al., "The structure of the extracellular domain of triggering receptor expressed on myeloid cells like transcript-1 and evidence for a naturally occurring soluble fragment", Journal of Biological Chemistry, May 2006, pp. 13396-13403, vol. 281, No. 19.
Morales et al., "Soluble TLT-1 modulates platelet-endothelial cell interactions and actin polymerization", Blood Coagulation & Fibrinolysis, Apr. 1, 2010, pp. 233-235, vol. 21, No. 3.
Barrow, et al., "Cutting edge: TREM-like transcript-1, a platelet immunoreceptor tyrosine-based inhibition motif encoding costimulatory immunoreceptor that enhances, rather than inhibits, calcium signaling via SHP-2", J Immunol, May 15, 2004, pp. 5838-5842;172(10).
Bleharski, et al., "A role for triggering receptor expressed on myeloid cells-1 in host defense during the early-induced and adaptive phases of the immune response", J Immunol. Apr. 1, 2003, pp. 3812-3818; 170(7).

(Continued)

*Primary Examiner* — James H Alstrum Acevedo
*Assistant Examiner* — Erinne Dabkowski
(74) *Attorney, Agent, or Firm* — Whitham Curtis Christofferson & Cook, PC

(57) ABSTRACT

Polypeptide The present invention relates to polypeptides fragments derived from the protein TLT-1 have been isolated and are useful in pharmaceutical preparations used for the treatment of inflammatory conditions such as sepsis.

12 Claims, 11 Drawing Sheets

(56) References Cited

OTHER PUBLICATIONS

Figure 1:
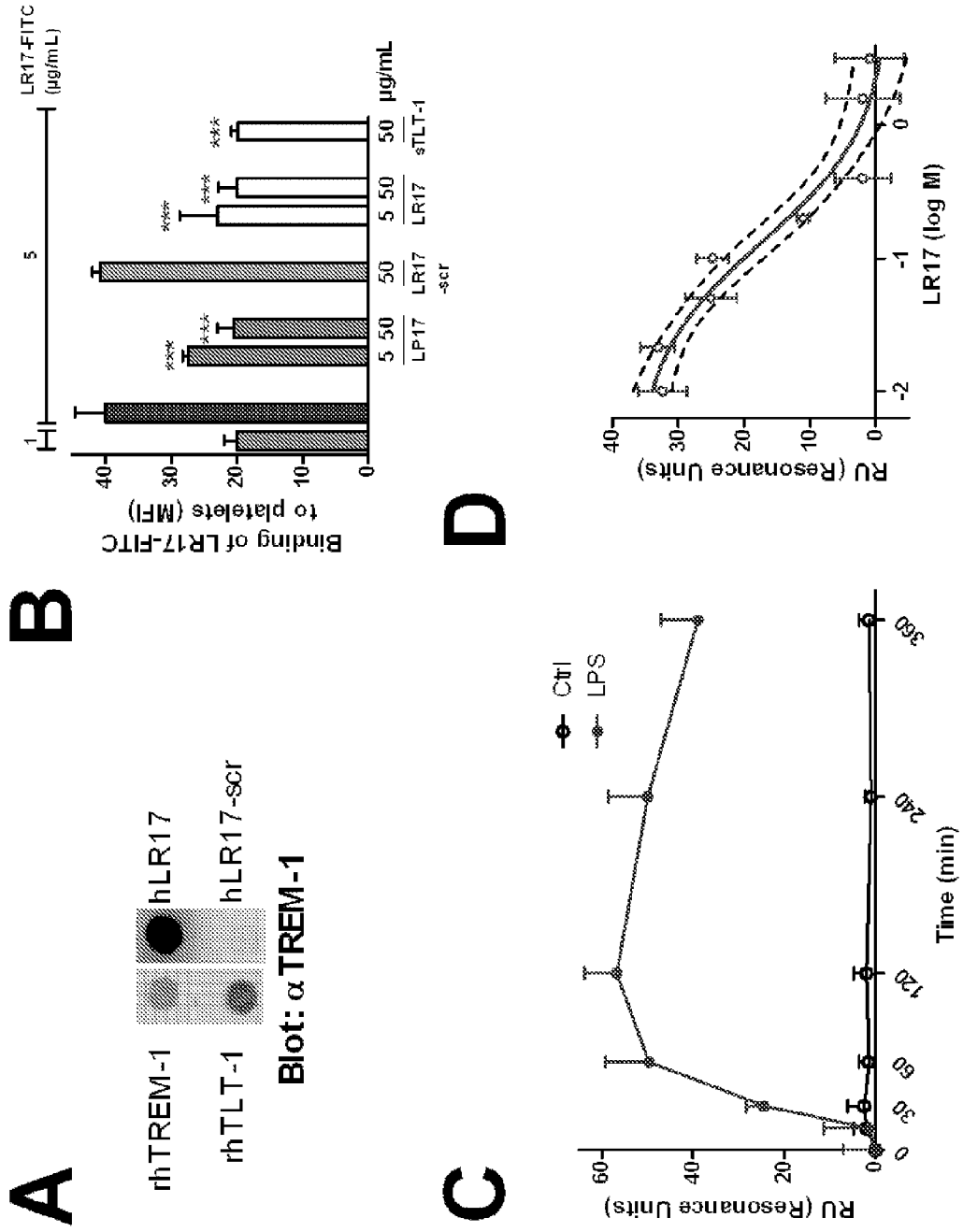

Bouchon, et al., "Cutting edge: inflammatory responses can be triggered by TREM-1, a novel receptor expressed on neutrophils and monocytes", J Immunol. May 15, 2000, pp. 4991-4995; 164(10).

Bouchon, et al., "TREM-1 amplifies inflammation and is a crucial mediator of septic shock", Nature. Apr. 26, 2001, pp. 1103-1107; 410(6832).

Gibot, et al., "Modulation of the triggering receptor expressed on the myeloid cell type 1 pathway in murine septic shock", Infect Immun. May 2006, pp. 2823-2830; 74(5).

Gibot, et al., "TREM-1 promotes survival during septic shock in mice", Eur J Immunol. Feb. 2007, pp. 456-466; 37(2).

Gibot, "Clinical review: role of triggering receptor expressed on myeloid cells-1 during sepsis", Critical Care. Oct. 5, 2005, pp. 485-489; 9(5).

Hara, et al., "The adaptor protein CARD9 is essential for the activation of myeloid cells through ITAM-associated and Toll-like receptors", Nature Immunology. Jun. 2007, pp. 619-629; 8(6).

Haselmayer, et al., "TREM-1 ligand expression on platelets enhances neutrophil activation", Blood. Aug. 1, 2007, pp. 1029-1035; 110(3).

Haselmayer, et al., "Signaling pathways of the TREM-1- and TLR4-mediated neutrophil oxidative burst", Journal of Innate Immunity. 2009, pp. 582-591; 1(6).

Kelker, et al., "Crystal structure of mouse triggering receptor expressed on myeloid cells 1 (TREM-1) at 1.76 A", J Mol Biol. Dec. 10, 2004, pp. 1175-1181; 344(5).

Kelker, et al., "Crystal structure of human triggering receptor expressed on myeloid cells 1 (TREM-1) at 1.47 A", J Mol Biol. Sep. 24, 2004, pp. 1237-1248; 342(4).

Washington, et al., "A TREM family member, TLT-1, is found exclusively in the alpha-granules of megakaryocytes and platelets", Blood. Aug. 15, 2004, pp. 1042-1047; 104(4).

Washington, et al., "Initial characterization of TREM-like transcript (TLT)-1: a putative inhibitory receptor within the TREM cluster", Blood. Nov. 15, 2002, pp. 3822-3824; 100(10).

\* cited by examiner

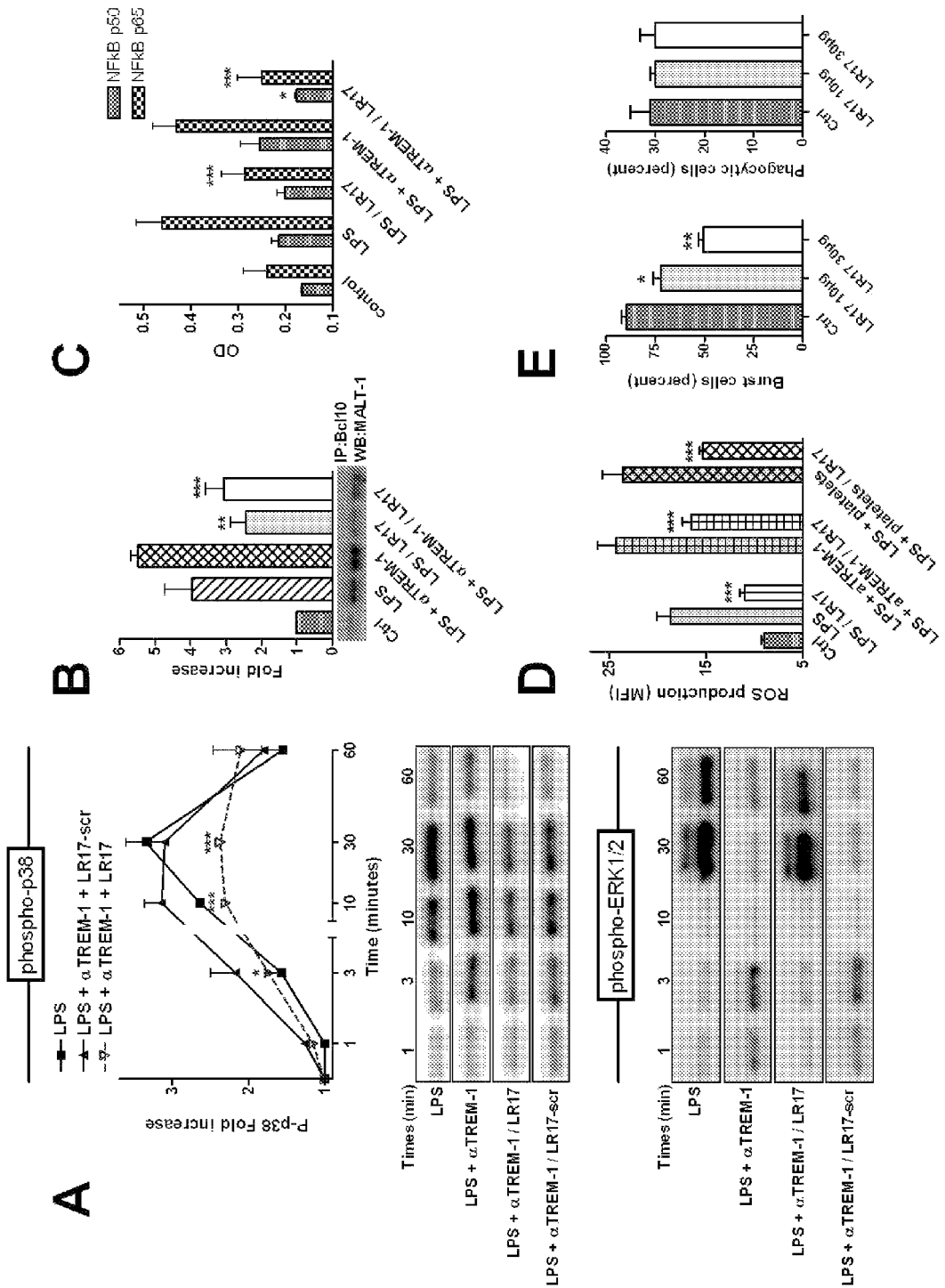
Figure 3 A, B, C, D, E

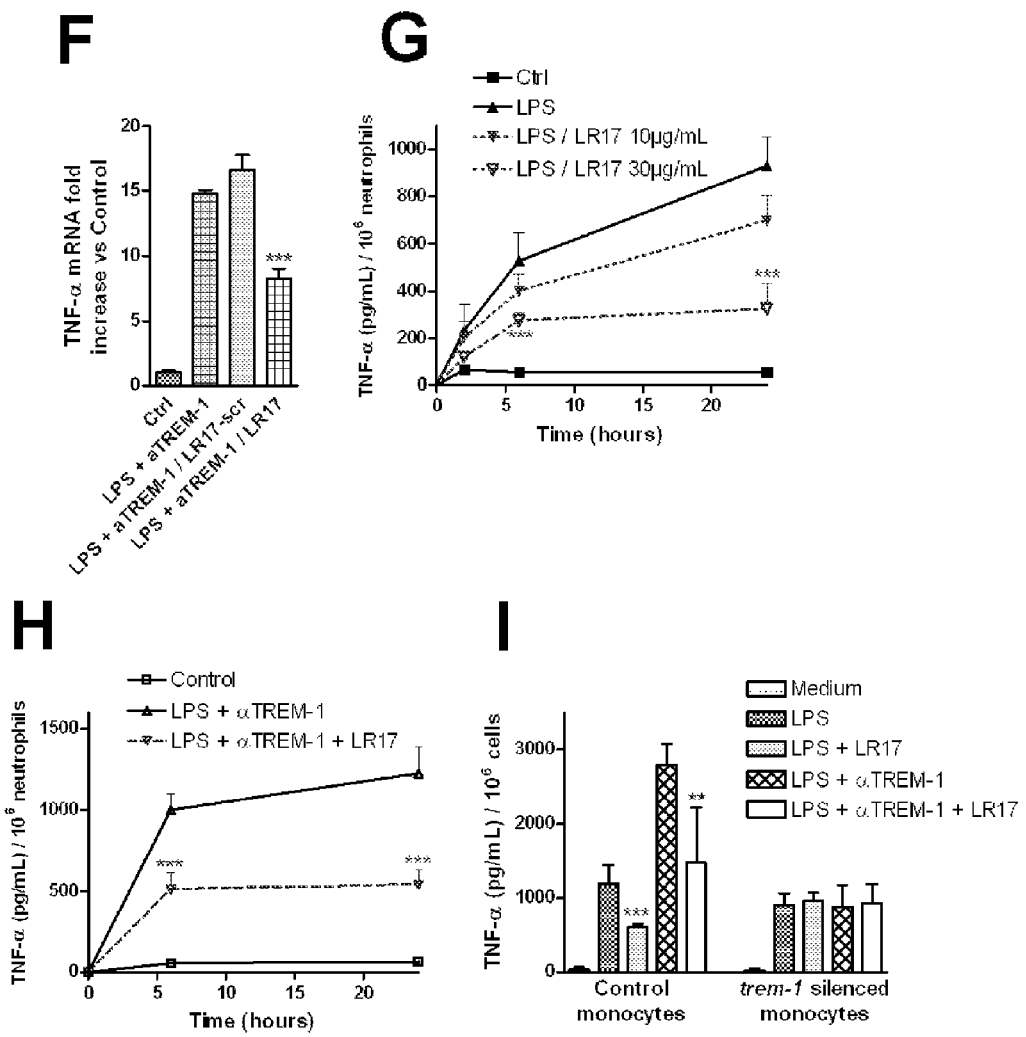
Figure 3 F, G, H and I.

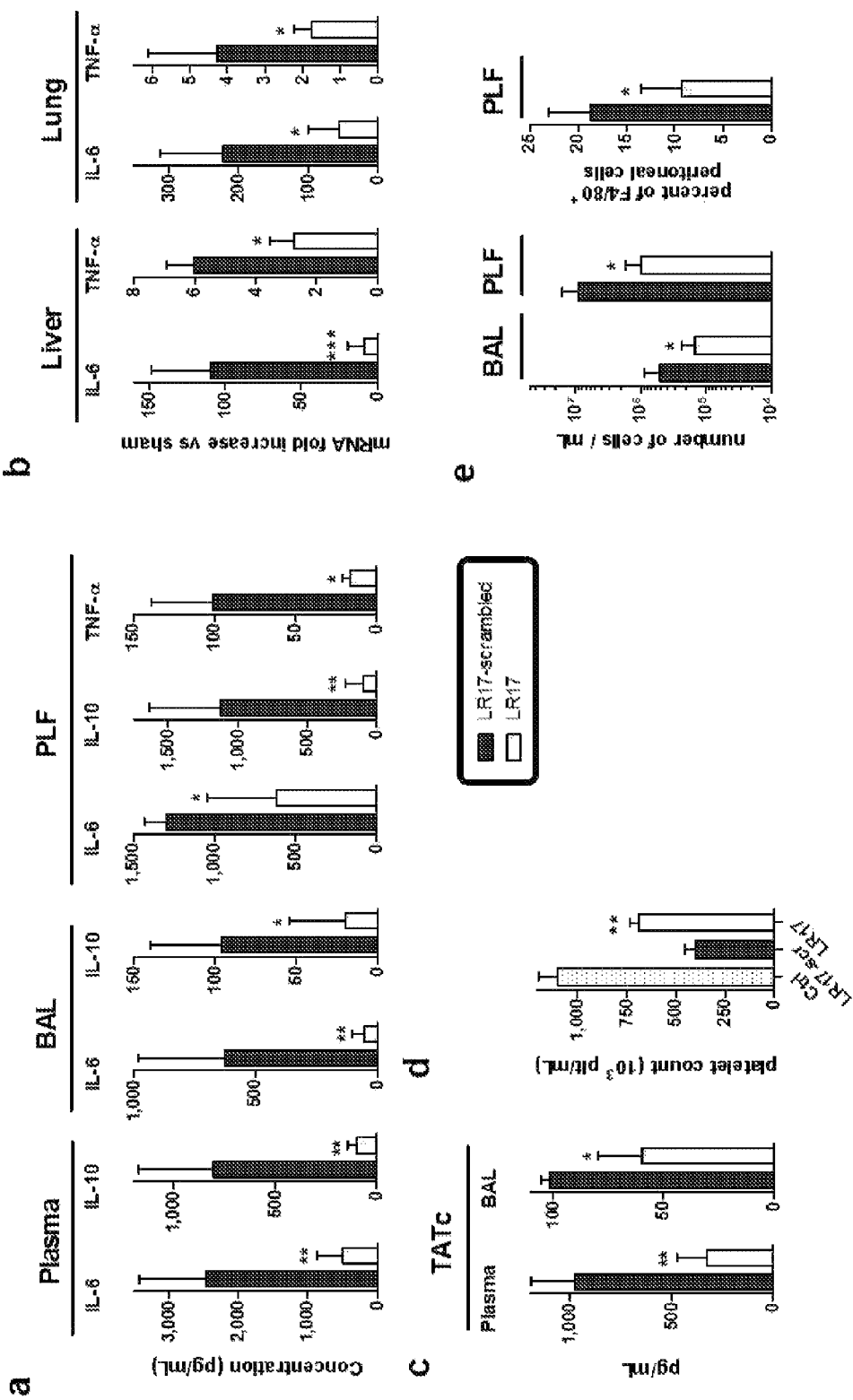
Figure 5 A, B, C, D, E

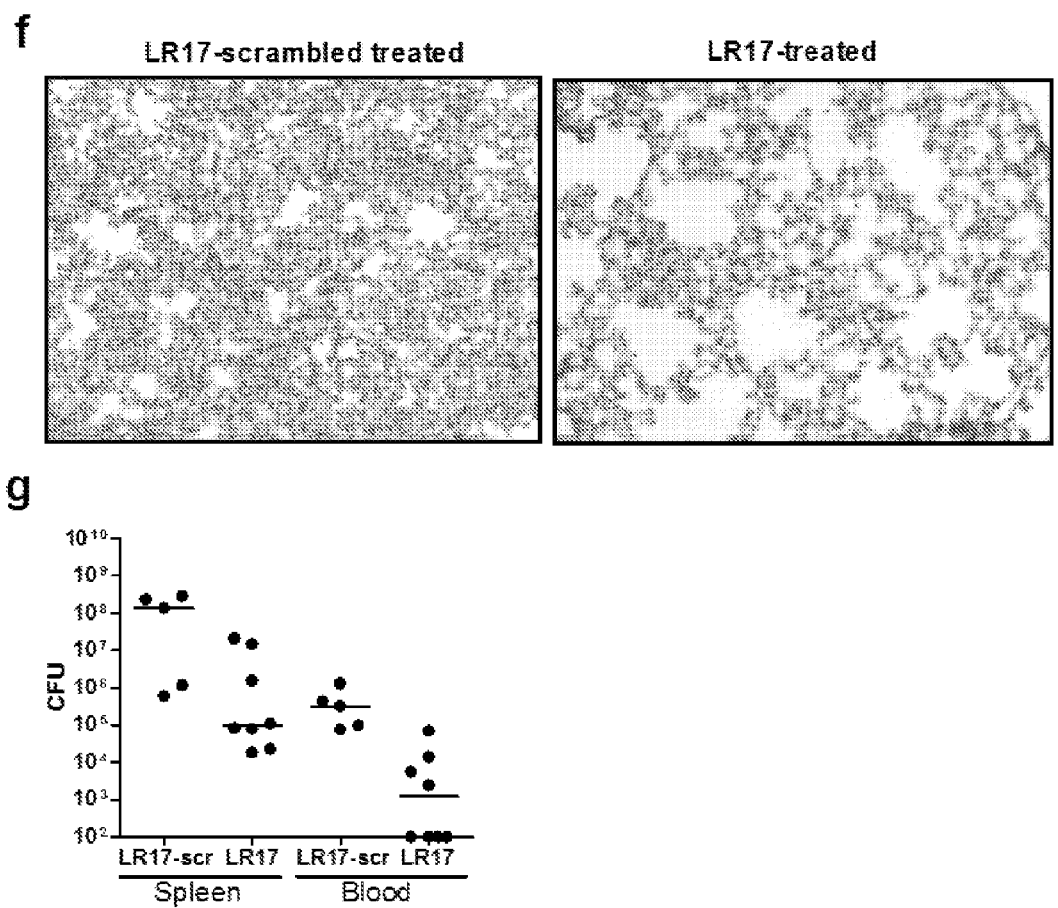
Figure 5 F, G

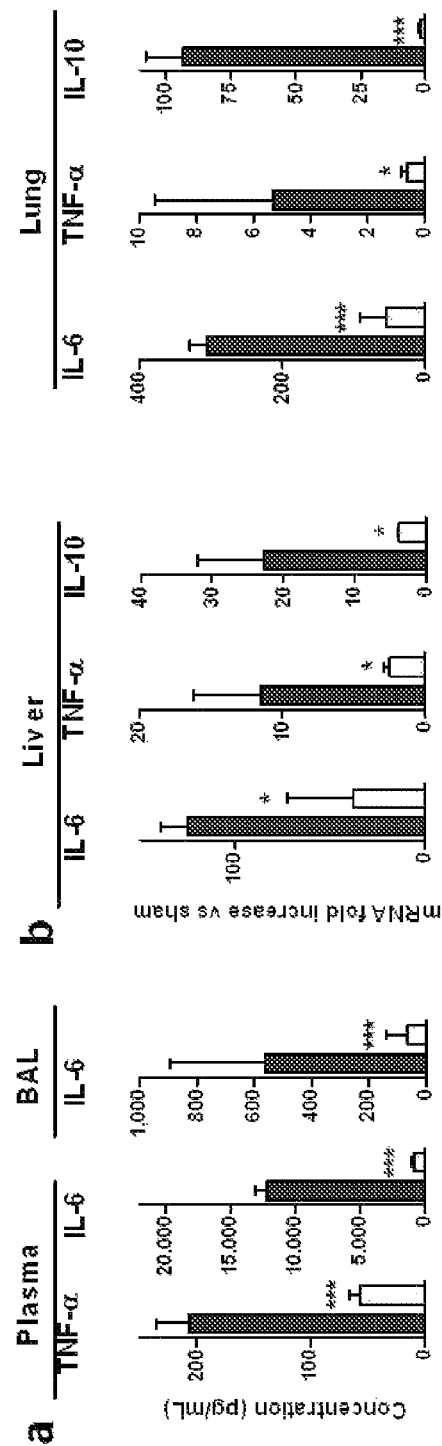
Figure 7 A and B

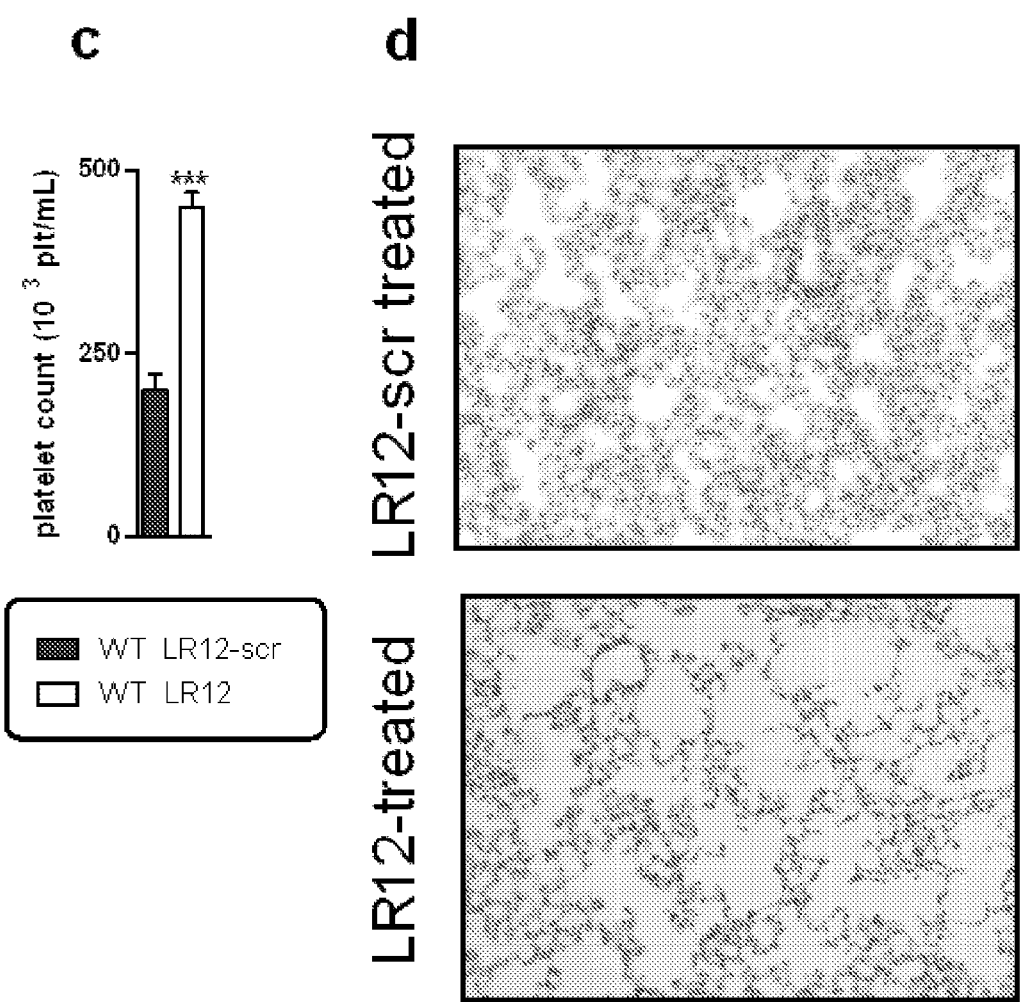
Figure 7 C and D

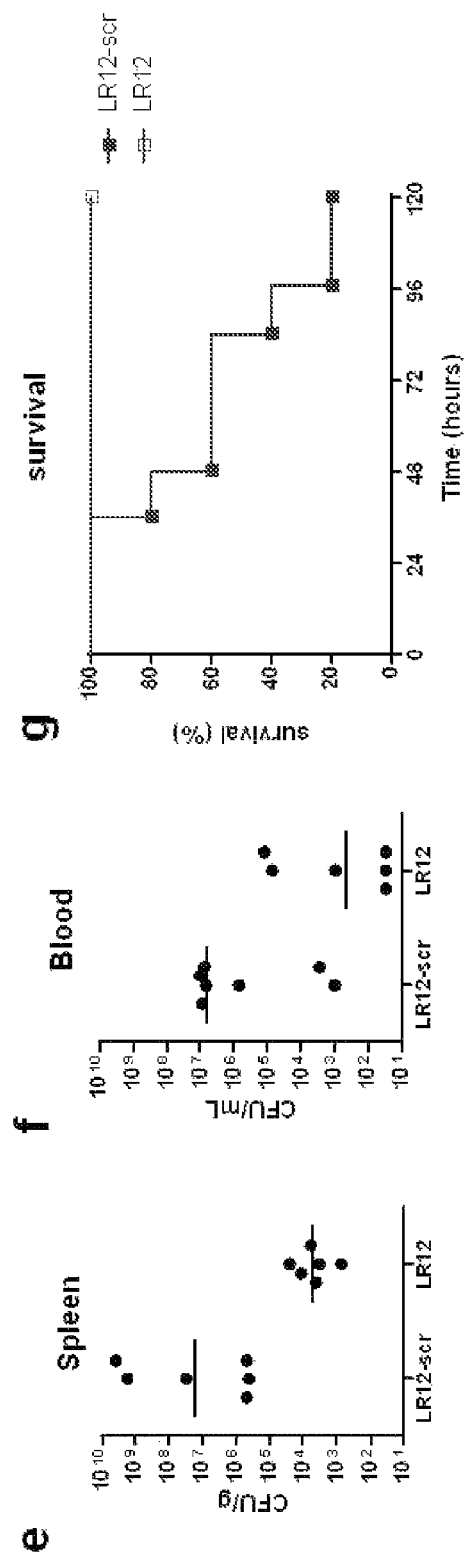
Figure 7 E, F and G

INHIBITING PEPTIDES DERIVED FROM TREM-LIKE TRANSCRIPT 1 (TLT-1) AND USES THEREOF

FIELD OF THE INVENTION

The present invention relates to polypeptides fragments derived from the protein TLT-1 and their uses for the treatment of inflammatory conditions and more particularly for the treatment of sepsis.

BACKGROUND OF THE INVENTION

Septic shock, a complex clinical syndrome that results from a harmful and damaging host response to infection, is the leading cause of mortality in intensive care units. Sepsis develops when the initial appropriate host response to systemic infection becomes dysregulated and over-amplified with an intimate crosstalk between inflammation and coagulation. Among candidates that act as amplifiers of the innate immune response, some belong to the Triggering Receptors Expressed on Myeloid cells (TREM) family [Bouchon, A., et al., 2000; Bleharski, J. R. et al., 2003; Haselmayer, P., et al., 2007; Gibot, S. et al., 2007]. The human TREM gene cluster is located on chromosome 6p21.1 and encodes six different proteins, TREM 1-5 and TLT-1 (TREM-Like Transcript-1). Human TREM-1 (hTREM-1) consists of an extracellular region of 194 amino acid (aa) residues, a membrane spanning region of 29 aa and a short cytoplasmic tail of 5 aa. The extracellular Ig-like domain contains the motif DxGxYxC which corresponds to a V-type Ig-domain. The Ig domain is connected to the transmembrane region by a 60-aa portion containing three N-glycosylation sites. The spanning region contains a Lys residue which forms a salt-bridge with an Asp residue of the transmembrane domain of an ITAM containing protein DAP 12, allowing the association between TREM-1 and its adaptor protein [Bouchon, A., et al., 2000; Kelker, M. S., et Al., 2004; Kelker, M. S. et al., 2004]. Engagement of TREMs triggers a signalling pathway involving ZAP70 and SYK and an ensuing recruitment and tyrosine phosphorylation of adaptor molecules such as GRB2, the activation of PI3K, PLC-γ, ERK-1, -2 and p38 MAPK [Haselmayer, P. et al., 2009; Gibot, S, 2005]. The activation of these pathways that ultimately leads to the activation of transcription factor NF-kB is regulated by CARD9-BCL10-MALT1 [Hara, H. et al., 2007]. Of note, although crystallographic analyses can predict TREM-1 recognition by using antibody-equivalent complementary determining regions (CDR) loops (such as TCRs, CD8 and CTLA-4), its natural ligand has yet to be determined.

Blocking experiments using a TREM-1 fusion protein or using a peptide designed to the CDR3 and the "F" β strand of the extracellular domain of TREM-1 demonstrated a reduced inflammation resulting in improved survival in murine models of endotoxemia and polymicrobial sepsis [Bouchon, A., et al., 2001; Gibot, S. et al., 2006].

The protective effects of modulating TREM-1 signalling are also evident in other models of acute (ischemia-reperfusion, pancreatitis, haemorrhagic shock) or chronic inflammation (inflammatory bowel diseases, inflammatory arthritis). All these studies suggest a role of TREM-1 in amplifying infectious or sterile inflammation.

In addition to TREM-1, the TREM gene cluster includes TREM-like Transcript 1 (TLT-1). TLT-1 is abundant, exclusively expressed on platelets and megakaryocytes, and is sequestered in the platelet α granules. Upon platelet activation, TLT-1 is translocated to the platelet surface [Washington, A. V. et al., 2004]. TLT-1 contains a v-set Ig type-extracellular domain, a transmembrane region and a cytoplasmic tail that comprises an immunoreceptor tyrosine-based inhibitory motif (ITIM) and a polyproline-rich domain. Unlike other TREM family members, TLT-1 does not couple to the DAP 12 activating chain whereas it has been shown to enhance Ca++ signalling in rat basophilic leukemia (RBL) cells, suggesting TLT-1 is a co-activating receptor [Barrow, A. D. et al., 2004].

The specificity of TLT-1 expression on platelets suggested that it should play a unique role in haemostasis and/or thrombosis. Indeed, it has been suggested that the modulation of TLT-1 may have several potential in modulating platelet function, thus preventing inflammatory-associated hypercoagulation (but not directly inflammation) or platelet-associated disorder (e.g. bleeding or clotting disorder) [Washington A V. et al., 2009]. This modulation could be mediated in a direct (by interfering with a TLT-1-ligand) or indirect way (by modulating the TLT-1 intracellular pathway).

The inventors report for the first time herein that TLT-1 and TLT-1 derived peptides exhibit anti-inflammatory properties by specifically inhibiting TREM-1 activity. Such peptides are able to dampen TREM-1 signalling and thus behave as naturally occurring TREM-1 inhibitors. They further demonstrate that the same peptides, as a consequence of the inhibition of TREM-1 and its intracellular pathway, also modulate in vivo the proinflammatory cascade triggered by infection, thus inhibiting TREM-1-associated hyper-responsiveness and ensuing organ damages and death during sepsis.

SUMMARY OF THE INVENTION

The invention is based on the discovery that TLT-1 and TLT-1 derived peptides are able to inhibit specifically TREM-1.

The inventors have first shown that human TLT-1 (hTLT-1) and hTLT-1 derived peptides are able to specifically recognize and bind to human TREM-1 ligand.

The inventors have also shown that, as a result of hTLT-1 and hTLT-1-derived peptides binding to hTREM-1 ligand, hTLT-1 and hTLT-1-derived peptides are able to decrease in vitro and in vivo hTREM-1-induced human-TREM-1-expressing-cells activation, characterized by a modulation of intracellular signalling (phosphorylation pathways), CARDS-MALT1-BCL10 complex formation, NF-κB activation (nuclear translocation), ROS production (Reactive Oxygen Species) and cytokine/chemokines expression (mRNA) and secretion (protein).

The inventors have also shown that TLT-1 derived peptides are able to treat TREM-1 associated disorders, ie diseases in which TREM-1 activation plays a role in the physiopathological process, like acute inflammatory disorders (sepsis, severe sepsis or septic shock, hemorrhagic shock, ischemia-reperfusion, pancreatitis) or chronic inflammatory disorders (inflammatory bowel diseases, rheumatic diseases, cancer).

Thus, the invention relates to a polypeptide fragment comprising at least 6 consecutive amino acids selected from the amino acid sequence SEQ ID NO 1 or a function-conservative variant for use in the treatment of an inflammatory condition.

A further object of the invention consists in a pharmaceutical composition that comprises at least one polypeptide as defined herein, or alternatively, a vector containing a nucleic acid that codes for a polypeptide of the invention.

DETAILED DESCRIPTION OF THE INVENTION

Definitions

Throughout the specification, several terms are employed and are defined in the following paragraphs.

As used herein, the term "TREM-1" for "Triggering receptor expressed on myeloid cells 1" denotes a cell-surface molecule that has been identified both on human and murine polymorphonuclear neutrophils and mature monocytes. It belongs to the immunoglobulin superfamily and activates downstream signalling pathways with the help of an adapter protein called DAP12. The expression of TREM-1 is greatly up-regulated on neutrophils and monocytes in the presence of such bacteria as *Pseudomonas aeruginosa* or *Staphylococcus aureus*, both in cell culture and in tissue samples from patients with infection. In striking contrast, TREM-1 is not up-regulated in samples from patients with non-infectious inflammatory diseases such as psoriasis, ulcerative colitis or vasculitis caused by immune complexes. Moreover, when TREM-1 is bound to its ligand, a synergistic effect of LPS and an amplified synthesis of the pro-inflammatory cytokines such as TNF-[alpha] are observed together with an inhibition of IL-10 production.

As used herein, the term "TLT-1" for "TREM-like transcript 1" denotes a member of the TREM family. The initial work from Mcvicar group [Washington A. V. et al., 2004] demonstrated that TLT-1 is abundant, specific to the platelet and megakaryocyte lineage, and is sequestered in the platelet a granules. Upon platelet activation with thrombin or LPS, TLT-1 is translocated to the platelet surface. TLT-1 contains a v-set Ig type-extracellular domain, a transmembrane region and a cytoplasmic tail that comprises an immunoreceptor tyrosine-based inhibitory motif (ITIM) and a polyproline-rich domain. Unlike other TREM family members, TLT-1 does not couple to the DAP 12 activating chain whereas it has been shown to enhance Ca$^{++}$ signalling in rat basophilic leukemia (RBL) cells, suggesting TLT-1 is a co-activating receptor. The amino acid sequence of TLT-1 is described as the amino acid sequence SEQ ID NO 1.

The polypeptides of the invention are described in the table 1 below.

TABLE 1 polypeptides of the inventions

| Polypeptide name | Sequence | SEQ ID |
|---|---|---|
| TLT-1-CDR2 | SAVDRRAPAGRR | SEQ ID NO 2 |
| TLT-1-CDR3 | CMVDGARGPQILHR | SEQ ID NO 3 |
| LR17 | LQEEDAGEYGCMVDGAR | SEQ ID NO 4 |
| TLT-1-LR17 scramble | GAEREVCMDEYGALQDG | SEQ ID NO 5 |
| LR6-1 | LQEEDA | SEQ ID NO 6 |
| LR6-2 | EDAGEY | SEQ ID NO 7 |
| LR6-3 | GEYGCM | SEQ ID NO 8 |
| LR12 | LQEEDAGEYGCM | SEQ ID NO 9 |

As used herein, the term "Function-conservative variants" denotes peptides derived from a polypeptide of the invention in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent of protein or amino acid sequence similarity between any two proteins of similar function may vary and may be, for example, from 70% to 99% as determined according to an alignment method such as by the Cluster Method, wherein similarity is based on the MEGALIGN algorithm. A "function-conservative variant" also includes a polypeptide which has at least 20% amino acid identity as determined by BLAST or FASTA algorithms, preferably 40% more preferably 60%, preferably at least 75%, most preferably at least 85%, and even more preferably at least 90%, and which has the same or substantially similar properties or functions as the native or parent protein to which it is compared.

As used herein, the term "derivative" refers to a variation of a polypeptide of the invention or of a function-conservative variant thereof that are otherwise modified, i.e. by covalent attachment of any type of molecule to the polypeptide, by addition of chemical compound in any of the amino-acids of the sequence, in order to modify in vitro or in vivo conformation, activity, specificity, efficacy or stability of the polypeptide.

As used herein, the terms "treating" or "treatment", denotes reversing, alleviating, inhibiting the progress of, or preventing the disorder or condition to which such term applies, or one or more symptoms of such a disorder or condition.

According to the invention the terms "pharmaceutically" or "pharmaceutically acceptable" denotes entities and compositions that do not produce an adverse, allergic or other non desired reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

According to the invention, the term "patient" or "individual" to be treated is intended for a human or non-human mammal (such as a rodent (mouse, rat), a feline, a canine, or a primate) affected or likely to be affected by inflammatory disorders. Preferably, the subject is a human.

Polypeptides and Uses Thereof

A first aspect of the invention relates to a polypeptide comprising at least 6 consecutive amino acid selected from the amino acid sequence SEQ ID NO 1 and a function-conservative variant.

In a preferred embodiment, the polypeptide according to the invention has a length of 6 to 20 amino acids, or 10 to 20 amino acids, or 12 to 18 amino acids or 14 to 16 amino acids.

In another embodiment, the polypeptide according to the invention comprises a 6 consecutive amino acid sequence selected from the group consisting of SEQ ID NO: 6, SEQ ID NO: 7 or SEQ ID NO: 8.

In another preferred embodiment, the polypeptide according to the invention comprises an amino acid sequence as set forth in SEQ ID NO: 9.

In another preferred embodiment, the polypeptide according to the invention comprises an amino acid sequence as set forth in SEQ ID NO: 4.

In another preferred embodiment, the polypeptide has an amino acid sequence selected from the amino acid sequences SEQ ID NO 2 or SEQ ID NO 3.

In another embodiment, the polypeptide according to the invention may have D- or L-configuration.

In another embodiment, the amino acid from the amino end of the polypeptide according to the invention has an acetylated terminal amino group, and the amino acid from the carboxyl end has an amidated terminal carboxy group. Therefore, the invention also includes derivatives of the peptide of the invention in which the amino-terminal end is acetylated or in which where the carboxy-terminal end is amidated.

In addition, the polypeptides according to the invention may undergo reversible chemical modifications in order to increase its bioavailability (including stability and fat solubility) and its ability to pass the blood-brain barrier and epithelial tissue. Examples of such reversible chemical modifications include esterification of the carboxy groups of glutamic and aspartic amino acids with an alcohol, thereby removing the negative charge of the amino acid and increasing its hydrophobicity. This Esterification is reversible, as the ester link formed is recognized by intracellular esterases which hydrolyze it, restoring the charge to the aspartic and glutamic residues. The net effect is an accumulation of intracellular polypeptide, as the internalized, de-esterified polypeptide cannot cross the cell membrane.

Another example of such reversible chemical modifications include the addition of a further peptidic sequence, which allows the increase of the membrane permeability, such as a TAT peptide or Penetratin peptide (see—Charge-Dependent Translocation of the Trojan. A Molecular View on the Interaction of the Trojan Peptide Penetratin with the 15 Polar Interface of Lipid Bilayers. Biophysical Journal, Volume 87, Issue 1, 1 Jul. 2004, Pages 332-343).

The polypeptides according to the invention may be obtained through conventional methods of solid-phase chemical polypeptide synthesis, following Fmoc and/or Boc-based 20 methodology (see Pennington, M. W. and Dunn, B. N. (1994). Peptide synthesis protocols. Humana Press, Totowa.).

Alternatively, the polypeptide according to the invention may be obtained through conventional methods based on recombinant DNA technology, e.g., through a method that, in brief, includes inserting the nucleic acid sequence coding for the polypeptide of the invention into an appropriate plasmid or vector, transforming competent cells for said plasmid or vector, and growing said cells under conditions that allow the expression of the polypeptide of the invention and, if desired, isolating and (optionally) purifying the polypeptide of the invention through conventional means known to experts in these matters. The nucleic acid sequence that codes for the polypeptide of the invention may be easily deduced from the correspondence that exists between the amino acids and the nucleotide codons that code for such amino acids. In this case, an additional object of the invention is an isolated nucleic acid sequence that codes for the polypeptide of the invention. In one particular embodiment, said nucleic acid is selected from single-strand DNA, double-stranded DNA, and RNA. Additional objects of this invention are plasmids and expression vectors that contain said nucleic acid sequence that codes for the polypeptide of the invention, as well as prokaryotic or eukaryotic cells that express the polypeptide of the invention. A review of the principles of recombinant DNA technology may be found, for example, in the text book entitled "Principles of Gene Manipulation: An 5 Introduction to Genetic Engineering," R. W. Old & S. B. Primrose, published by Blackwell Scientific Publications, 4th Edition (1989).

As described, the invention also includes polypeptides which are functionally equivalent to the polypeptides of the invention or "function-conservative variant". In the sense used in this description, the expression "functionally equivalent" means that the peptide in question has at least one of the biological activities of the peptide of the invention, such as, for example, the ability to decrease the inflammation.

The capacity to decrease the inflammation of the polypeptides of the invention will become evident to the skilled person by implementing a simple test to evaluate the decrease of inflammation due to the polypeptides. For example, $5 \times 10^5$ isolated human neutrophils are incubated in presence of 100 ng/mL LPS and 10 µg/mL anti-TREM-1 mAb with or without 20 µg/mL of polypeptide for 24 hours at 37° C./5% $CO_2$. Supernatant is then collected and TNF-α and IL-6 concentrations measured by ELISA. If the studied peptide inhibits TREM-1, cytokine concentrations must decrease by up to 30% or more as compared to LPS+mAb without peptide.

Nucleic Acids, Vectors and Recombinant Host Cells

A second aspect of the invention relates to a nucleic acid molecule encoding polypeptides according to the invention.

In a preferred embodiment, the nucleic acid molecule encoding for a polypeptide which has a sequence SEQ ID NO 2, SEQ ID NO 3, SEQ ID NO 4, SEQ ID NO 6, SEQ ID NO 7, SEQ ID NO 8 or SEQ ID NO 9.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid molecules may be obtained by conventional methods well known to those skilled in the art, in particular by site-directed mutagenesis of the gene encoding the native protein. Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

The terms "vector", "cloning vector" and "expression vector" mean the vehicle by which a DNA or RNA sequence (e.g. a foreign gene) may be introduced into a host cell, so as to transform the host and promote expression (e.g. transcription and translation) of the introduced sequence.

Any expression vector for animal cell may be used, as long as a gene encoding a polypeptide or chimeric derivative of the invention can be inserted and expressed. Examples of suitable vectors include pAGE107, pAGE103, pHSG274, pKCR, pSG1 beta d2-4 and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or 30 viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882, 877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

Another object of the invention is also a prokaryotic or eukaryotic host cell genetically transformed with at least one nucleic acid molecule according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

Preferably, for expressing and producing the polypeptides, and in particular the polypeptide according to the invention, eukaryotic cells, in particular mammalian cells, and more particularly human cells, will be chosen.

Typically, cell lines such as CHO, BHK-21, COS-7, C127, PER.C6 or HEK293 25 could be used, for their ability to process to the right post-translational modifications of the derivatives.

The construction of expression vectors in accordance with the invention, the transformation of the host cells can be carried out using conventional molecular biology techniques. The V-ATPase c-subunit derivatives of the invention, can, for example, be 30 obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention.

Therapeutic Methods, Uses and Pharmaceutical Compositions

A third object of the present invention relates to a polypeptide according to the invention for use in the treatment of an inflammatory condition.

Inflammatory conditions according to the invention including but are not limited to allergies, asthma, myopathies, cancer, inflammatory arthritis, inflammatory bowel diseases, acute respiratory distress syndrome (ARDS), avian influenza, smallpox, and systemic inflammatory response syndrome (SIRS), severe acute respiratory syndrome (SARS), ischemia and reperfusion syndromes, hemorrhagic shock.

Inflammatory conditions according to the invention including but are not limited to sepsis, severe sepsis, septic shock, hemorrhagic shock, ischemia-reperfusion or pancreatitis.

In a preferred embodiment, the inflammatory condition is sepsis.

The polypeptide according to the invention is able to treat inflammatory condition through its properties of decoy receptor.

By "decoy receptor", is meant that the polypeptides according to the invention trap the TREM-1 ligand and prevent its physiological effects on TREM-1.

The polypeptides according to the invention could therefore form part of a combined therapy (aimed at several therapeutic targets) with the objective of more effectively stopping sepsis.

An additional object of this invention is a pharmaceutical composition which includes a therapeutically effective amount of at least one polypeptide according to the invention, along with at least one pharmaceutically acceptable excipient. In one particular embodiment, said pharmaceutical composition also contains one or more (COOH) peptides. Alternatively, the pharmaceutical composition of the invention may contain a therapeutically effective amount of a vector that contains at least one nucleic acid sequence that codes for a polypeptide of the invention, along with at least one adjuvant and/or a pharmaceutically acceptable excipient. Said vector may be used in gene therapy.

By a "therapeutically effective amount" is meant a sufficient amount of the chimeric derivative of the invention to treat inflammatory condition at a reasonable benefit/risk ratio applicable to any medical treatment.

It will be understood that the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active products of the invention (polypeptides or vectors) may be administered for the treatment of inflammatory conditions, manifested, for example, by redness, increased heat, swelling, pain, and loss of function.

The therapeutically effective amount of the active product of the invention [peptides or vectors (constructions)] that should be administered, as well as the dosage for the treatment of a pathological condition with the peptides and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the peptides or vectors (constructions) of the invention may be in any form that is suitable for administration, e.g., solid, liquid or semi-solid, such as creams, ointments, gels or solutions, and these compositions may be administered by any suitable means, for example, orally, parenterally, inhalation or topically, so they will include the pharmaceutically acceptable excipients necessary to make up the desired form of administration. A review of the different pharmaceutical forms for administering medicines and of the excipients necessary for obtaining same may be found, for example, in the "Tratado de Farmacia Gal nica" (Treatise on Galenic Pharmacy), C. Faul i Trillo, 1993, Luz n 5, S.A. Ediciones, Madrid.

In the pharmaceutical compositions of the present invention for oral, sublingual, subcutaneous, intramuscular, intravenous, transdermal, local, pulmonary or rectal administration, the active principle, alone or in combination with another active principle, can be administered in a unit administration form, as a mixture with conventional pharmaceutical supports, to animals and human beings. Suitable unit administration forms comprise oral route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptides according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variations in dosage will necessarily occur depending on the conditions of the subject being treated. The person responsible for administration will, in any event, determine the appropriate dose for the individual subject.

The polypeptide of the invention may be formulated as a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

As previously mentioned, the peptides according to the invention could form part of a combined therapy for the purpose of more effectively stopping inflammatory. In this case, the invention provides a pharmaceutical composition that includes at least one peptide of the invention; along with another or other inflammatory inhibiting compound(s) for example non-steroidal anti-inflammatory compounds.

An additional object of this invention relates to the polypeptides of the invention or of vectors that contain at least one sequence that codes for a polypeptide of the invention for the treatment of inflammatory condition including but not limited to allergies, asthma, myopathies, cancer, acute respiratory distress syndrome (ARDS), sepsis, avian influenza, smallpox, and systemic inflammatory response syndrome (SIRS), severe acute respiratory syndrome (SARS).

In addition, the invention provides a method for the treatment of inflammatory conditions in mammals which consists of administering to said mammal suffering from said pathological disease a therapeutically effective amount of at least one polypeptide of the invention, or of a vector containing at least one DNA sequence that codes for a polypeptide of the invention, preferably in the form of a pharmaceutical composition that contains it. In one particular embodiment of this invention, said pharmaceutical composition contains, in addition to the peptide or peptides of the invention, one or more (COOH) peptides.

Screening Methods

Another object of the invention relates to a method for screening a compound which invalidates the TREM-1 protein.

In particular, the invention provides a method for screening an inhibitor of the TREM-1 protein for the treatment of an inflammatory condition.

For example, the screening method may measure the binding of a candidate compound to TREM-1 protein, or to cells or membranes bearing the TREM-1 protein or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist).

In a particular embodiment, the screening method of the invention comprises the step consisting of:

a) providing a plurality of cells expressing the TREM-1 ligand protein and cells expressing the TREM-1 protein:
b) incubating said cells with a candidate compound;
c) determining whether said candidate compound binds to the TREM-1 ligand protein; and
d) selecting the candidate compound that inhibits the TREM-1/TREM-1 ligand interaction.

Neutrophils produce Reactive oxygen species in presence of LPS, anti-TREM-1 mAb, or platelets (that constitutively express the TREM-1 ligand) with a synergistic effect of these different inducers that is mediated by neutrophils membrane-bound TREM-1. We expect a reduction of ROS production when neutrophils are incubated in presence of some peptides that inhibit the TREM-1/TREM-1 ligand interaction.

ROS production can be easily quantified by using a fluoregenic substrate (DCFDA: 5-(and -6)-carboxy-2',7'-dichlorodihydrofluorescein diacetate (carboxy-H2DCFDA)*mixed isomers*). For example, $2.5 \times 10^5$ isolated human neutrophils are incubated 2 hours at 37° C./5% $CO_2$ with 5 µM of DCFDA, in presence of 20 µg/mL anti-TREM-1 mAb with or without 100 ng/mL LPS. ROS production by TREM-1 activation and its modulations by polypeptides is thus quantified by flow cytometry: if the studied peptide inhibits TREM-1, mean fluorescence intensity (MFI) must decrease as compared to conditions without TREM-1 mAb.

This rapid assay will allow us to determine the best TREM-1 inhibiting peptides in order to further study them in other experiments such as NF-kB activation, cytokine production, protein phosphorylation.

In general, such screening methods involve providing appropriate cells which express the TREM-1 protein, its orthologs and derivatives thereof on their surface. In particular, a nucleic acid encoding the TREM-1 protein may be employed to transfect cells to thereby express the TREM-1 protein. Such a transfection may be achieved by methods well known in the art.

In a particular embodiment, cells are selected from the group consisting of immune cells involved in cytokine and inflammatory mediator release including but not limited to monocytes/macrophages, and neutrophils.

The screening method of the invention may be employed for determining an inhibitor by contacting such cells with compounds to be screened and determining whether such compound invalid or not the TREM-1 protein.

According to a one embodiment of the invention, the candidate compound may be selected from a library of compounds previously synthesized, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. No. 5,475,096 and U.S. Pat. No. 5,270,163. Further illustratively, the candidate compound may be selected from the group of antibodies directed against the PP1/GADD34 complex.

The invention will be further illustrated by the following figures and examples. However, these examples and figures should not be interpreted in any way as limiting the scope of the present invention.

FIGURES

FIG. 1: LR17 specifically binds to the TREM-1 ligand.

For these experiments, we used LR17-scrambled as a control randomized-sequence peptide.

(A) Immunoblot of rhTLT-1, rhTREM-1, LR17 and LR17-scrambled revealed by mouse anti-TREM-1 mAb (TREM-1 agonist).

(B) Flow cytometry analysis of FITC-labelled LR17 (1 or 5 µg/mL) binding to TREM-1 ligand expressed on resting or thrombin-activated (5 UI/mL) human platelets is reversed by co-incubation with unlabelled LR17, sTLT-1 or LP17, a TREM-1 derived peptide.

(C-D) Surface plasmon resonance assays of LPS-stimulated neutrophils supernatants to a rsTREM-1-coated sensorship in absence (C) or presence (D) of LR17.

Figure 2:
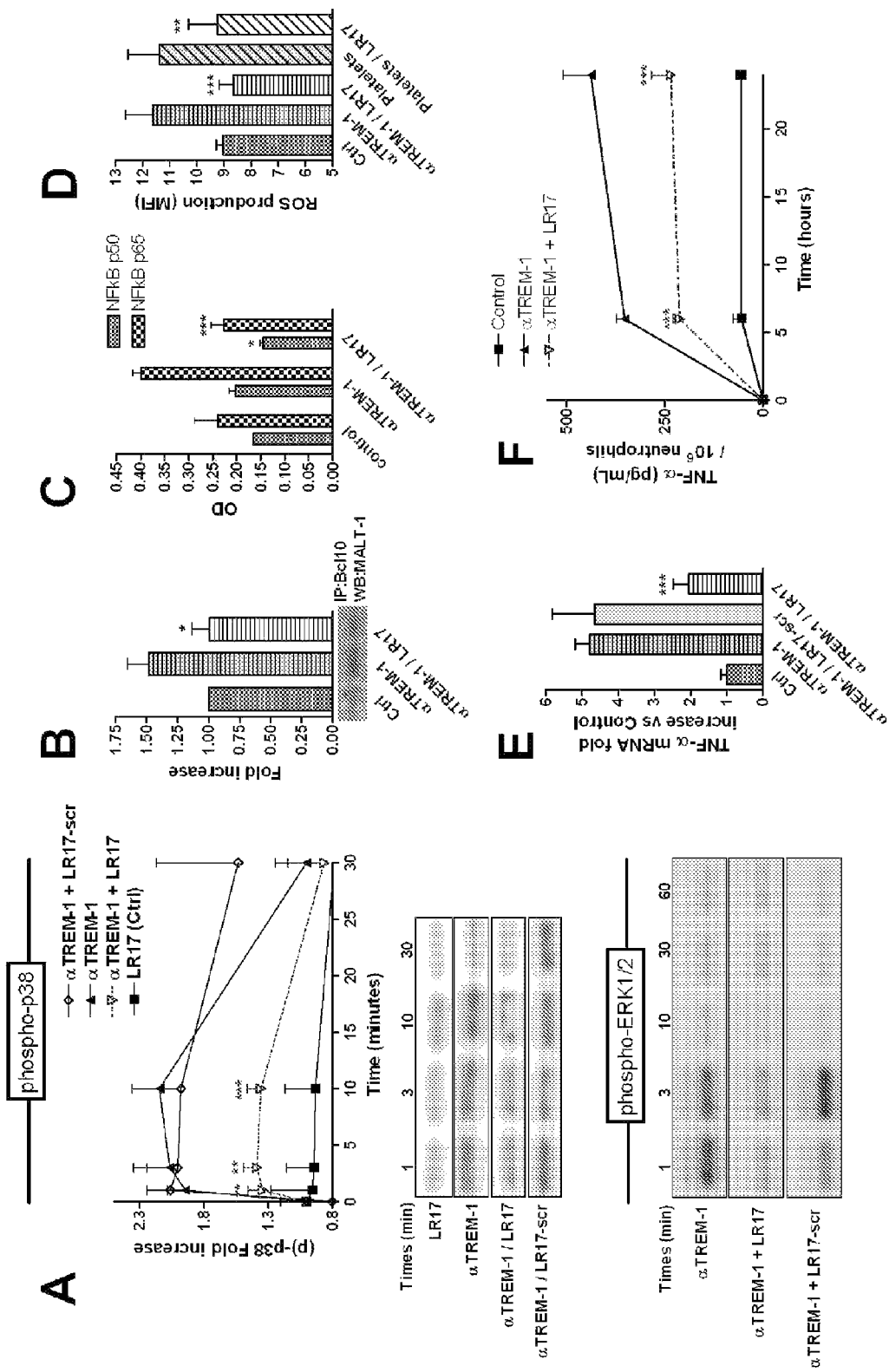

FIG. 2: LR17 specifically inhibits TREM-1 activation by trapping its ligand, acting like a decoy receptor.

For these experiments, isolated human neutrophils were stimulated with TREM-1 agonist (αTREM-1, 5 µg/mL) with or without LR17 (30 µg/mL) or control LR17-scrambled peptide (30 µg/mL) at indicated times. Data are representative of at least 5 different experiments. Results are mean±SD. p values are *p<0.001 p<0.01 *p<0.05 [αTREM-1+LR17] versus [αTREM-1].

(A) Activation of TREM-1 phosphorylation pathway: Western Blot of lysates of neutrophils stimulated for 1, 3, 10, 30 and 60 minutes, analysed with antibody to phospho (p)-p38 and (p)-ERK1/2.

(B) CARDS-MALT1-BCL10 complex formation: Immunoblot of MALT-1 after immunoprecipitation with anti-BCL10 mAb of lysates of neutrophils stimulated for 20 minutes.

(C) NF-κB nuclear translocation: ELISA of nuclear p50 and p65 NF-kB subunits of neutrophils treated for 2 hours.

(D) ROS production: Flow cytometric quantification (DCFDA reduction) of neutrophils ROS production after 2 hours stimulation.

(E) Cytokines expression: TNF-α mRNA levels in neutrophils stimulated for 6 hours.

(F) Cytokines production: ELISA of TNF-α in neutrophils treated for 2, 6 and 24 hours FIG. 3: LR17 exhibits anti-inflammatory properties by decreasing LPS- or LPS and αTREM-1-induced cellular activation.

For these experiments, isolated human neutrophils or monocytes were stimulated with LPS (0.1 μg/mL) and TREM-1 agonist (αTREM-1, 5 μg/mL) with or without LR17 (30 μg/mL) or control LR17-scrambled peptide (30 μg/mL), at indicated times. Data are representative of at least 5 different experiments. Results are mean±SD. p values are *p<0.001 p<0.01 *p<0.05 [LPS/LR17] versus [LPS] or [LPS+αTREM-1/LR17] versus [LPS+αTREM-1].

(A) Western Blot of lysates of neutrophils stimulated for 1, 3, 10, 30 and 60 minutes, analysed with antibody to phosphor (p)-p38 and (p)-ERK1/2.

(B) CARD9-MALT1-BCL10 complex formation: Immunoblot of MALT-1 after immunoprecipitation with anti-BCL10 mAb of lysates of neutrophils stimulated for 20 minutes.

(C) NF-κB nuclear translocation: ELISA of nuclear p50 and p65 NF-kB subunits of neutrophils treated for 2 hours.

(D) ROS production: Flow cytometric quantification (DCFDA reduction) of neutrophils ROS production after 2 hours stimulation.

(E) Quantitative determination of neutrophil phagocytosis and oxidative burst induced by *E. Coli* was performed by flow cytometry. sTLT-1/LR17 showed no action on PMA- or fMLP-induced oxidative burst (not shown). Data (mean±SD) are representative of 6 different experiments.

(F) Cytokines expression: TNF-α mRNA levels in neutrophils stimulated for 6 hours.

(G-H) Cytokines production: ELISA of TNF-α in neutrophils treated for 2, 6 and 24 hours.

(I) ELISA of TNF-α produced by native or Trem-1 silenced human monocytes.

Figure 4:
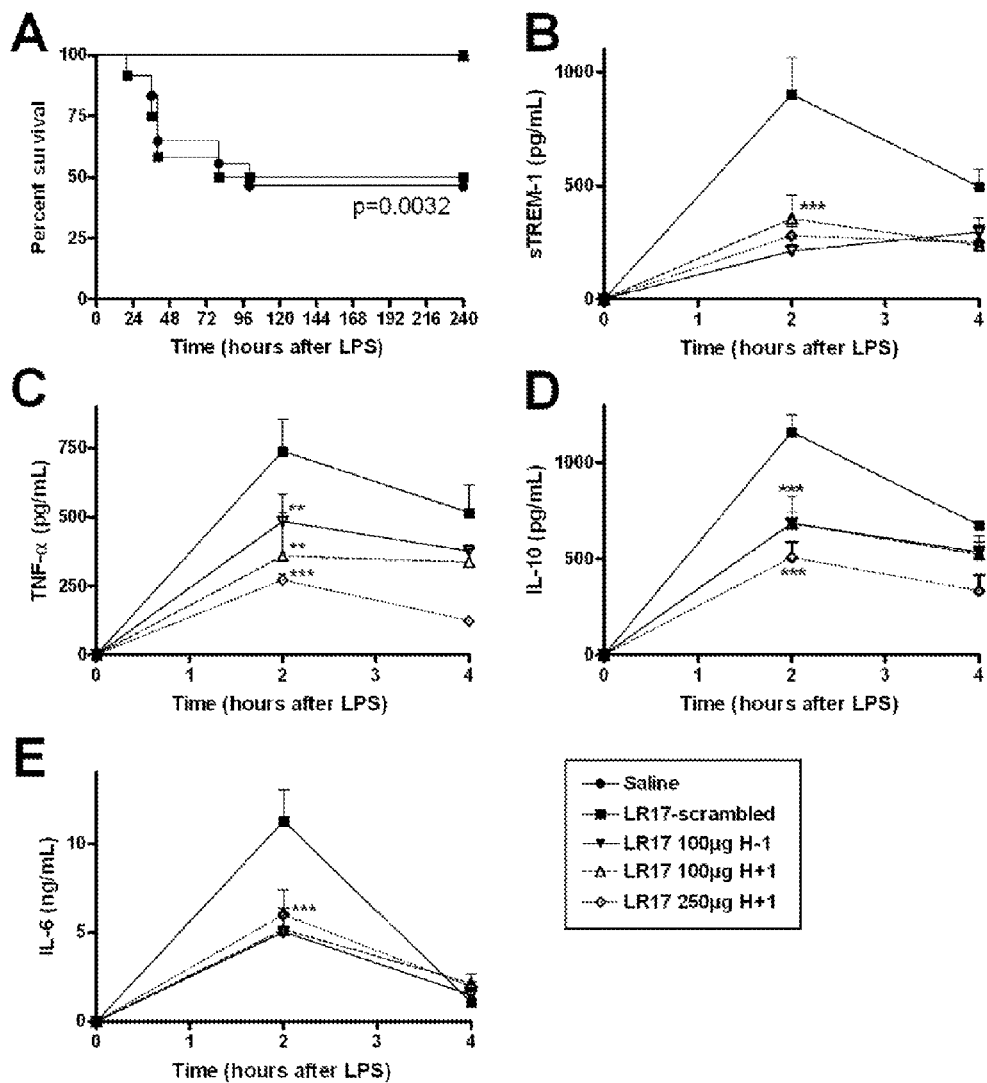

FIG. 4: LR17-associated TREM-1 modulation protects endotoxemic mice from death and systemic response.

Male Balb/c mice (20-23 g) were randomly grouped (15 mice per group) and treated with an LD50 of LPS. LR17 (100 μg or 250 μg in 0.2 mL NaCl 0.9%), scrambled-LR17 (100 μg in 0.2 mL NaCl 0.9%), or 0.2 mL NaCl 0.9% was administered 60 min before or 60 minutes after LPS. 4-6 animals per group were sacrificed upon penthotal overdose at 2 and 4 hours after LPS injection and blood was sampled through cardiac puncture. Results are mean±SD. p values are *p<0.05, p<0.01, *p<0.001 compared with control animals.

(A) LR17 treatment confers a survival advantage as shown by the survival curve (Log Rank test, p=0.0032) with no differences between doses or injection times of LR17.

(B-E) ELISA of plasma TNF-α, IL-6, IL-10 and sTREM-1.

FIG. 5: LR17-associated TREM-1 modulation protects mice against polymicrobial sepsis.

Adult male Balb/c mice (20-23 g) were subjected to caecal ligation and puncture under isoflurane anaesthesia and were randomly grouped (n=5-10 per group) to receive a single LR17 (100 μg in 0.2 mL NaCl 0.9%), scrambled-LR17 (100 μg in 0.2 mL NaCl 0.9%), or 0.2 mL NaCl 0.9% i.p. injection. After 24 hours, animals were killed under anaesthesia. Results are mean±SD. p values are *p<0.05, p<0.01, *p<0.001 compared with control animals.

(A) ELISA of TNF-α, IL-6, an IL-10 in the plasma, the peritoneal and the broncho-alveolar lavage fluids.

(B) q-PCR mRNA quantification of IL-6 and TNF-α in lung and liver.

(C) ELISA of plasma and broncho-alveolar lavage fluids TATc.

(D) Platelet count in whole blood.

(E) Cell counts in the peritoneal and broncho-alveolar lavage fluids.

(F) Histopathological examination of the lungs 24 hours after the CLP. Intra-alveolar hemorrhage, protein precipitation, and leukocyte infiltration into the alveoli, and edematous thickening of perivascular space were attenuated in the LR17-treated mice. A typical illustration (×10) is shown here.

(G) Bacterial counts form the spleens and blood obtained 24 hours after the CLP.

Figure 6:
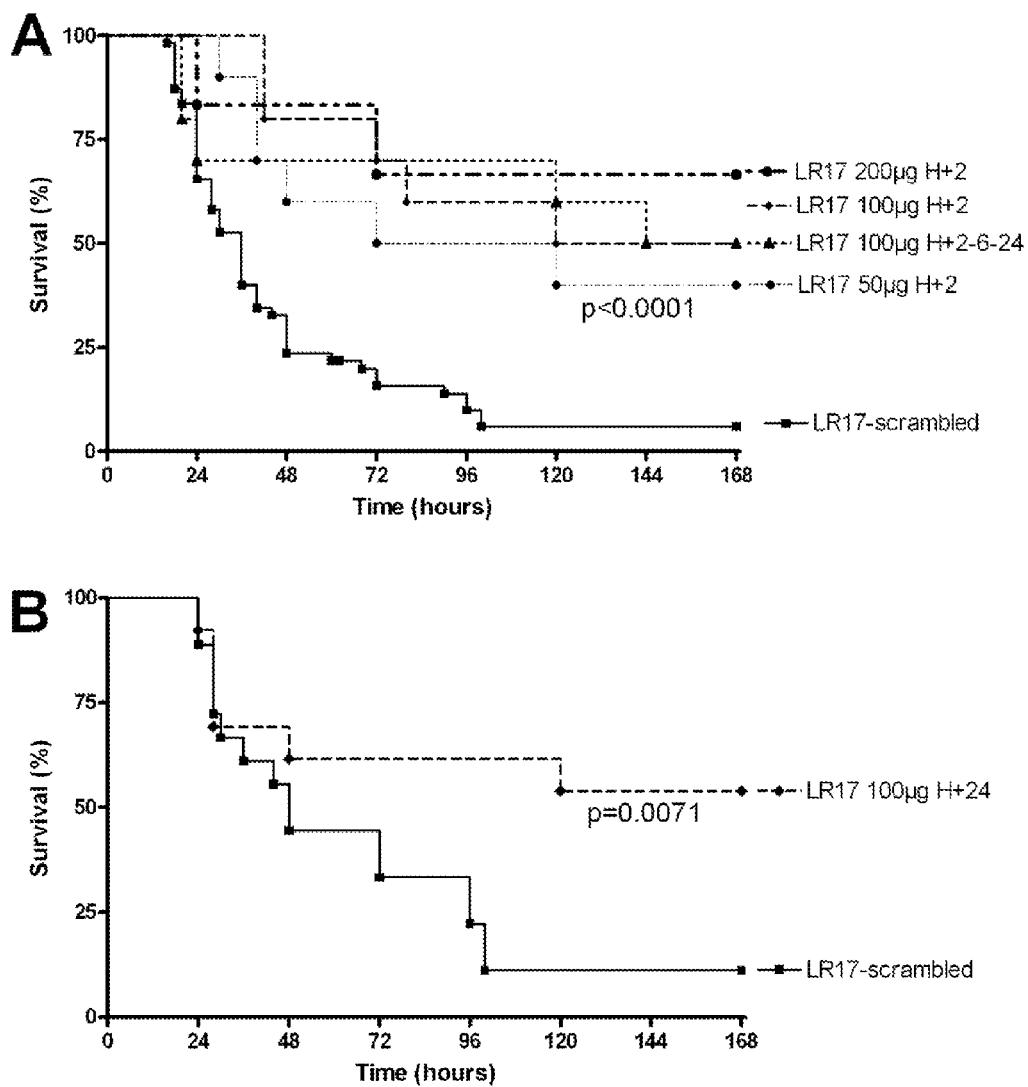

FIG. 6: LR17-associated TREM-1 modulation protects mice from CLP-induced mortality.

(A-B) Adult male Balb/c mice (20-23 g) were subjected to caecal ligation and puncture under isoflurane anaesthesia and were randomly grouped (n=25-40 per group) to receive a LR17, scrambled-LR17, or 0.2 mL NaCl 0.9% i.p. injection at indicated times. Survival was monitored over 1 wk and analyzed by Log Rank test. LR17 conferred a significant protection even when administered 24 hours after the onset of sepsis.

FIG. 7: LR12-associated TREM-1 modulation protects mice against polymicrobial sepsis.

(a) TNF-α and IL-6 concentrations in plasma and BAL.

(b) Lung and liver IL-6, TNF-α and IL-10 mRNA quantification.

(c) Platelet count in whole blood.

(d) Histopathological examination of the lungs 24 h after CLP.

(e-f) Bacterial counts in spleen and blood obtained 24 h after CLP.

(g) Survival curves after CLP analyzed by Log Rank test.

Results are expressed as mean±SD. p values are *p<0.05, p<0.01, *p<0.001 compared with control animals.

EXAMPLE

Material & Methods

Surface Plasmon Resonance.

Detection of TREM-1-ligand on LPS-stimulated neutrophils supernatants was assessed by binding to a recombinant soluble form of TREM-1 (rsTREM-1) coated on a CM5 sensor chip with the BIAcore X instrument at 25° C. with a flow rate of 5 μL/min. Binding specificity was verified through competition with the soluble rsTREM-1. Inhibition of TREM-1-ligand binding by LR17 was assessed.

Peptides.

Based on the TLT-1 and TREM-1 sequences in GenBank|EMBL|DDBJ (accession numbers AY078502, AF534822, AF241219 and AF287008), TLT-1-peptides were designed mimicking different parts of its extracellular domain: TLT-1-CDR2 (SAVDRRAPAGRR, SEQ ID No 2), TLT-1-CDR3 (CMVDGARGPQILHR, SEQ ID No 3), and a well conserved sequence between TREM-1 and TLT-1: TLT-1-LR17 (LQEEDAGEYGCMVDGAR, SEQ ID No 4), TLT-1-LR12 (LQEEDAGEYGCM, SEQ ID NO: 9), LR6-1 (LQEEDA), LR6-2 (EDAGEY) and LR6-3 (GEYGCM). They were chemically synthesized (Pepscan Presto BV, Lelystad, The Netherland) as a COOH terminally amidated peptide for in vitro and in vivo assays, and FITC-labelled for flow cytometry experiments. The correct peptides were obtained with >99% yields and were homogeneous after preparative purification, as confirmed by mass spectrometry and analytic reversed-phase high-performance liquid chromatography. These peptides were free of endotoxin. A scrambled peptide containing the same amino acids of TLT-1-LR17 but in a totally different sequence order were synthesized and served as control peptide (TLT-1-LR17 scramble: GAEREVCMDEYGALQDG, SEQ ID No 5).

Isolation and Stimulation of Human PMNs and Monocytes.

Human peripheral blood samples were collected on EDTA from healthy volunteer donors originating from laboratory staff.

PMNs were isolated by a Sodium Diatrizoate 13.8%/Dextran 500 8.0% density gradient (polymorphprep, AbCys). Monocytes were isolated by negative cell-sorting of PB-MNCs by Monocytes Isolation Kit II (Miltenyi). Cells were then washed twice with PBS (BioMerieux) and resuspended in complete medium (RPMI 1640 containing 100 UI/mL penicillin, 100 µg/mL streptomycin, 0.25 µg/mL Amphotericin B and 10% FCS, Eurobio) before stimulation. Purity was assessed by flow cytometry (anti-CD45, -CD14 and -CD66b, Beckman Coulter).

Platelets Isolation.

Acid Citrate Dextrose blood samples were centrifuged (100 g, 10 min) to obtain Platelet-Rich Plasma. PRP was then centrifuged (550 g, 10 min) over a 36% (wt/vol) BSA gradient and platelets collected from the interphase before being washed in Tyrode's salts buffer (Sigma-Aldrich) supplemented with 5 mM EGTA. For activation, platelets were incubated for 30 minutes with 5 U/mL thrombin (Sigma-Aldrich) or 1 µg/mL E. Coli LPS (0111:B4, Sigma-Aldrich) at 37° C. and subsequently fixed with 2% (wt/vol) paraphormaldehyde (PFA, Sigma-Aldrich). Residual PFA was removed by two additional washing steps in Tyrode buffer. Activation was assessed by anti-CD62P (Beckman Coulter).

Cell Stimulation.

Depending on the experiment, cells were stimulated in complete medium supplemented with 100 ng/mL of E. Coli LPS (0111:B4, Sigma-Aldrich), anti-TREM-1 mAb (R&Dsystems) and TLT-1-peptides at different times and concentrations on 96-wells plates (Greiner Bio One). Supernatants were collected for cytokine measurements and cells subjected to flow cytometry or lysed for protein phosphorylation analyses and NFkB activity measurement.

FACS Analysis.

Isolated cells (neutrophils, monocytes or platelets) were blocked for a specific binding with 10% human Ig (Sigma-Aldrich) for 1 hour on ice. Cells were incubated with recombinant soluble FITC-labelled TLT-1-peptides, FITC-labelled LP17 (or corresponding FITC-labelled scrambled peptides), PE-labelled anti-TREM-1 mAb (R&Dsystems), CD62P-FITC, CD66b-PE, CD45-PE, CD14-FITC (all from Beckman Coulter)

Cytokine Concentration Measurement.

Cytokines in supernatants of stimulated human cells or mouse plasma were measured by ELISA (human and mouse Quantikine ELISA kits, R&Dsystems) and cytokines panel assays (Proteome Profiler Human Cytokine Array Kit, Panel A and Proteome Profiler Mouse Cytokine Array Kit, Panel A, R&Dsystems) according to manufacturers' recommendations.

Protein Phosphorylation Analysis.

Stimulated PMNs were lysed at 1, 3, 10, 30 and 60 minutes with PhosphoSafe Extraction Reagent (Novagen) and centrifuged for 5 minutes at 16,000 g at 4° C. to collect the supernatant. Protein concentration was determined according to Bradford's method (Pierce). Lysates were then analysed by Western Blot (Criterion XT Bis-Tris Gel, 4-12%, BioRad and PVDF membrane, Millipore), revealed with anti-phospho-p38 and -pERK1/2 and corresponding secondary antibody conjugated with horse-radish peroxidase (Cell Signaling) and SuperSignal West Femto Substrate (Pierce). Anti-p38 and -ERK1/2 were used for normalization. Alternatively, PMNs were analyzed after 20 minutes of stimulation for a panel of multiple phosphorylated proteins by immunoblot (Human Phospho-Kinase Array, R&Dsystems). Acquisition and quantitative signals density analyses were done by LAS-4000 imager and Multi-Gauge software (Fujifilm).

Immunoprecipitation.

Cells were lysed with CytoBuster Protein Extraction Reagent (Novagen). Samples were normalized by total protein concentration and lysates were pre-cleared before performing Immunoprecipitation. Pre-cleared lysates were then incubated overnight at 4° C. with rabbit-anti-Bcl10 mAb (Cell Signaling) or rabbit-anti-CARD9 (Antibodies Online). Thereafter, anti-rabbit-Ig beads (eBioscience) were added for 1 hour at room temperature. Beads were then washed 3 times, denatured in Laemli buffer 5 minutes at 95° C. and centrifuged at 16,000 g for 1 min. Supernatant containing retained proteins was analysed by western blotting and revealed with anti-Malt-1 and corresponding secondary antibody HRP-conjugated (Cell Signaling).

NF-kB Activity Measurement.

Stimulated cells were collected, nuclear extracts obtained by nuclear extraction kit and NFkB activity measured with human p50/p65 combo transcription factor assay kit (Cayman Chemical) following the manufacturers' instructions.

ROS Production Assessment.

The quantitative determination of neutrophil phagocytosis and oxidative burst was performed by flow cytometry using the Phagotest and the Bursttest (Orpegen Pharma, Heidelberg, Germany) following the manufacturers' recommendations. A FITC-labelled opsonized E. coli was used to determine the general phagocytic activity (ingestion of one or more bacteria per cell) and the individual cellular phagocytic activity (number of bacteria per cell). For evaluation of oxidative burst activity, unlabeled opsonized E. coli, fMLP, PMA LPS and activated- or non-activated-platelets (30:1) were used as stimulants and DCFDA as a fluoregenic substrate (Invitrogen) accordingly with manufacturers' instructions.

Preparation of Trem-1 Knock-Down Monocytes.

TREM-1 silencing was performed with Human Monocyte Nucleofector Kit (Amaxa) using siRNA sequences obtained from Qiagen. Isolated monocytes were electroporated with siRNA (without siRNA and with siRNA without electroporation as negative control, and with a GFP-reporter plasmid for positive control) and cultured for 24 hours in Human Monocyte Nucleofector Medium (Amaxa) before stimulation. TREM-1 expression was then assessed by quantitative RT-PCR and flow cytometry 24 hours after transfection. Medium was changed and monocytes were stimulated with LPS, anti-TREM-1 mAb and TLT-1-peptides for 24 hours. Therefore, medium was collected for cytokine measurement.

LPS-Induced Endotoxemia in Mice.

After approval by the local ethical committee, male Balb/c mice (4-6 weeks) were randomly grouped and treated with LPS i.p. in combination with LR17 (in 250 µL normal saline) or LR17-scrambled 1 hour before or after LPS challenge. The viability of mice was examined every hour, or animals were killed at regular intervals. Serum samples were collected by cardiac puncture and assayed for cytokines and sTREM-1 levels by ELISA (R&Dsystems).

Caecal Ligation and Puncture (CLP) Polymicrobial Sepsis Model.

Male Balb/c mice (4-6 weeks) were anesthetized with isoflurane. The cecum was exposed through a 1.0 cm abdominal midline incision and subjected to a ligation of the distal half followed by one puncture with a G21 needle. A small amount of stool was expelled from the puncture to ensure patency. The cecum was replaced into the peritoneal cavity and the abdominal incision closed in two layers. After surgery, all mice were injected s.c. with 0.5 mL of 0.9% NaCl solution for fluid resuscitation. The animals were randomly grouped and treated LR17 or LR17-scrambled as control in 25 µL 0.9% NaCl solution and administered i.p. In order to determine the effect of various doses of LR17 at different times, mice were treated with 50, 100 or 200 µg of LR17 at H1 after surgery, or with 3 injections of 100 µg at 2, 6 and 24 hours or with 100 µg in one injection at 24 hours after CLP and then monitored for survival. Five additional animals per group were killed under anaesthesia at 24 h after CLP for the determination of bacterial count and cytokines levels. Peritoneal lavage fluid was obtained using 2 mL RPMI 1640 (EuroBio), and blood was collected by cardiac puncture. Concentrations of plasma cytokines were determined by ELISA (R&Dsystems). For the assessment of bacterial counts, blood and crushed spleen were plated in serial log dilutions on tryptic soy supplemented with 5% sheep blood agar plates. After plating, tryptic soy agar plates were incubated at 37° C. aerobically for 24 h and anaerobically for 48 h. Results are expressed as CFU per ml of blood or per gram of spleen.

Results

LR17 Specifically Binds to the TREM-1 Ligand

To determine whether sTLT-1 may specifically bind to the TREM-1 ligand and thus interfere with the TREM-1/TREM-1 ligand interaction, we used a specific TREM-1 agonist known to bind and activate TREM-1, mimicking TREM-1 engagement by its ligand. We observed that as control, TREM-1 itself was able to recognize its ligand (agonist) but not the control LR-17 scrambled peptide, and that sTLT-1 and LR17 were also able to bind the TREM-1 ligand (FIG. 1 A).

Human platelets are known to constitutively express TREM-1 ligand. We thus wanted to directly confirm the interaction between sTLT-1 and the TREM-1 ligand in studying the fixation of LR17 on platelets. We observed that FITC-labelled LR17 binds both to resting and thrombin-activated platelets. This binding was decreased by co-incubation with LP17, a TREM-1 derived peptide known to binds to TREM-1 ligand. The opposite holds true: FITC-labelled LP17 binding to platelets was decreased by co-incubation with rsTLT-1 or LR17, but not by LR17-scrambled. LR17 did not bind to neutrophils or monocytes, known to not expressing TREM-1 ligand (FIG. 1B).

Although neutrophils do not express a membrane bound TREM-1 ligand, these cells may release its soluble form. Using surface plasmon resonance we observed that LPS-activated neutrophils time-dependently secrete a TREM-1 ligand (FIG. 1 C). LR17 was able to block the binding of the TREM-1 ligand to immobilized TREM-1 (FIG. 1D) suggesting that sTLT-1 could interfere with TREM-1/TREM-1 ligand interactions Taken together, these results suggest that LR17 is able to specifically bind and trap TREM-1 ligand, suggesting it could acts as a decoy receptor and inhibit TREM-1 ligand/TREM-1 interaction.

LR17 Inhibits TREM-1 Activation and Decreases TREM-1-Mediated Neutrophils Activation.

Engagement of TREM-1 on myeloid cells leads to p38 MAPK and ERK 1/2 phosphorylation. This effect was partly abrogated by LR17 (FIG. 2 A). Phosphoprotein arrays also showed that phosphorylation of proteins involved in the TREM-1 signalling (mTOR, Lyn, AKT, MSK1/2, MEK 1/2, GSK 3α/β, RSK, and p53) was also reduced in presence of LR17 (data not shown). TREM-1 signals through DAP 12 association, an ITAM containing adaptor protein. As the formation of CARDS-BCL10-MALT1 has been proved essential in linking ITAM coupled receptors to downstream NF-kB activation, we next wanted to examine the effect of LR17 on this complex assembly. As expected, TREM-1 activation was associated with an increased CARDS-MALT1-BCL10 complex formation. This effect was reversed by LR17 (FIG. 2 B). TREM-1 signalling pathway finally leads to NF-kB activation. Again, LR17 decreased anti-TREM-1 induced NF-kB activity (FIG. 2 C). As a readout for TREM-1 induced cell activation, we chose ROS production. Both TREM-1 agonist and platelets (that express TREM-1 ligand) have been shown to increase ROS production by neutrophils. We observed that this production was partly prevented in presence of LR17 (FIG. 2 D). Finally, LR17 was able to decrease cytokine production by activated neutrophils, both at the gene and protein levels for TNF-α (FIGS. 2 E and F), IL-6 and IL-8 (data not shown).

Therefore, these results further support the fact that LR17 is a naturally occurring, direct inhibitor of TREM-1.

LR17 Exhibits Anti-Inflammatory Properties by Decreasing LPS- or LPS and αTREM-1-Induced Cellular Activation.

TREM-1 modulation has been shown to reduce TLR-mediated neutrophil activation. TLR4 engagement upon LPS stimulation leads to NF-kB activation and ROS production by neutrophils. Indeed, LR17 decreased LPS-associated (with or without αTREM-1) phosphorylation of p38 and ERK1/2 (FIG. 3A), CARD9-MALT1-BCL10 complex formation (FIG. 3B), NF-κB translocation (FIG. 3 C) and intracellular ROS production (FIG. 3D). LR17 also decreased neutrophil oxidative burst mediated by E. coli. By contrast, sTLT-1 and LR17 did not alter neutrophils' phagocytic properties (FIG. 3 E).

As expected, αTREM-1 induced TNF-α production by neutrophils. This effect was abrogated by the addition of LR17. Anti-TREM-1 also synergized with LPS for cytokine production: once again, this synergy was blocked by LR17.

Finally, LPS associated TNF-α secretion by neutrophils and monocytes were dose-dependently reduced in presence of LR17, both at the gene and protein level. αTREM-1 synergized with LPS in inducing cytokines production: once again, this effect was abrogated by the addition of LR17 (FIGS. 3 F, G, H and I). The same holds true for IL-6 and IL-8 (not shown). Using broad cytokine arrays, we confirmed a decreased production of TNF-α, IL-6 and IL-8, but also of GRO-α, IL-10, IL-16, MCP-1, MIP-1β and RANTES by LR17. All these effects were also confirmed to occur in human monocytes and upon TLR2 (Pam3SK4) (not shown) stimulation.

To conclusively demonstrate that sTLT-1 modulates the LPS-induced inflammatory response via TREM-1, the effect of LR17 on monocytes treated with Trem-1 siRNA was investigated. Trem-1 silencing was achieved in monocytes with more than 90% efficiency from 24 to 96 hours after transfection as verified by RT-qPCR. Silenced monocytes were also stimulated with LPS/anti-TREM-1 mAb: although silenced monocytes responded normally to LPS, anti-TREM-1 mAb did not induce TNF-α production. Concomitantly, LR17 did not show any effect on TNF-α synthesis by silenced monocytes (FIG. 3I).

These results further support the hypothesis that sTLT-1 is a naturally occurring inhibitor of TREM-1.

LR17 Protects Endotoxemic Mice from Death

We next wanted to elucidate whether sTLT-1 could have some protective effects during sepsis. Adult male Balb/c mice were i.p. administered with a single dose of LR17, LR17-scrambled or NaCl 0.9% 60 min before LPS administration (LD50, 25 mg/kg). All LR17-treated animals survived (FIG. 4a). To investigate whether LR17 treatment could be delayed until after the administration of LPS, we injected LR17 beginning 1 hour after LPS injection. This delayed treatment conferred significant protection (FIG. 4a). No late death occurred over 10 days, indicating that LR17 did not merely delay the onset of LPS lethality but provided lasting protection. Control mice all developed lethargy, piloerection, and diarrhea before death. By contrast, LP17-treated mice remained well groomed and active, had no diarrhea, and were lively. To clarify the mechanism by which LR17 protected mice from LPS lethality, we determined the serum levels of TNF-α, IL-6, IL-10 and sTREM-1 of endotoxemic mice at 2 and 4 h. Compared with controls, pre- as well as post-treatment by LR17 reduced cytokines (FIG. 4b-e). Using a higher dose of LR17 (250 μg) did not confer advantage over the 100 μg dose.

LR17 Protects Mice Against Polymicrobial Sepsis

To investigate the role of LR17 in a more relevant model of septic shock, we performed CLP experiments. The control groups comprised mice injected with normal saline or with the control peptide (scrambled LR17). We first measured plasma IL-6 and IL-10 concentrations 24 hours after surgery. Both cytokines concentrations were decreased in LR17 (100 μg i.p. 2 hours after surgery)-treated animals (FIG. 5a). IL-6 and IL-10 were also decreased in the broncho-alveolar lavage fluid after LR17 treatment, as well as in the peritoneal lavage fluid (FIG. 5a). Screening of plasma levels of various cytokines using a cytokine array showed a decreased concentration of several other important inflammatory cytokines (C5a, IL-1ra, IL16, MCP-1, MIP-1α, MIP-2). Coagulation activation often occurs during sepsis as part of the inflammatory response. Both D-dimer and TATc plasma and alveolar concentrations were markedly elevated in the CLP mice. These coagulation abnormalities were prevented by LR17 (FIG. 5b).

Next, we investigated whether LR17 affects local cell recruitment both at the site of infection (the peritoneum) and distally (alveolar space). Indeed, cell infiltration was reduced by LR17 treatment at both sites (FIG. 5c). Histological study revealed severe lung injury, i.e., intra-alveolar hemorrhage, protein precipitation, and leukocyte infiltration into the alveoli, and edematous thickening of perivascular space in the septic mice. These alterations were attenuated in the LR17-treated animals (FIG. 5d). Therefore, LP17 prevents from the massive cellular infiltration and histological damage induced by peritonitis. We finally studied the effect of LR17 on bacterial clearance. As expected, we observed very high bacterial counts in the spleens of CLP mice 24 hours after the onset of the peritonitis. Moreover all control animals were found bacteriemic. By contrast, LR17 improved bacterial clearance and almost completely prevented septicaemia (FIG. 5e).

LR17 treatment was therefore able to modulate sepsis induced inflammatory response both locally and systemically, and to improve bacterial clearance.

LR17 Protects Mice from CLP-Induced Mortality

We investigated whether the modulation of the inflammatory response conferred by LR17 was able to translate into survival improvement during sepsis. In this CLP model of model of polymicrobial sepsis, LR17 conferred a dose-dependent significant protection against lethality even when administered as late as 24 h after the onset of sepsis. Interestingly, repeated injections of LR17 were not superior to single dose administration (FIG. 6).

LR12-Associated TREM-1 Modulation Protects Mice Against Polymicrobial Sepsis.

LR12 is a 12 amino-acids derived from LR17, composed of the N-terminal 12 amino-acids from LR17. When LR12 was administered to septic mice, it still conferred significant protection on systemic, broncho-alveolar and organ inflammation (FIGS. 7a and b), coagulation disorders (FIG. 7c), organ dysfunction (FIG. 7d), bacterial clearance (FIGS. 7e and f) and finally improved survival rate (FIG. 7g).

These results suggest that LR12 keeps same protective effect and efficacy than LR17.

Peptides of 6 Amino Acids (LR6-1, LR6-2 and LR6-3) Protect Mice Against Polymicrobial Sepsis.

LR6-1, LR6-2 and LR6-3 are 6 amino-acids derived from LR17 (Table 1). The peptides are administered to septic mice as described for LR17 and LR12 (see supra). Protection on systemic, broncho-alveolar and organ inflammation, coagulation disorders, organ dysfunction, bacterial clearance and survival rate are evaluated to investigate whether these peptides keep same protective effect and efficacy than LR12 and LR17.

REFERENCES

Throughout this application, various references describe the state of the art to which this invention pertains. The disclosures of these references are hereby incorporated by reference into the present disclosure.

Barrow, A. D. et al. Cutting edge: TREM-like transcript-1, a platelet immunoreceptor tyrosine-based inhibition motif encoding costimulatory immunoreceptor that enhances, rather than inhibits, calcium signaling via SHP-2. J. Immunol 172, 5838-5842 (2004).

Bleharski, J. R. et al. A role for triggering receptor expressed on myeloid cells-1 in host defense during the early-induced and adaptive phases of the immune response. J. Immunol 170, 3812-3818 (2003).

Bouchon, A., Facchetti, F., Weigand, M. A. & Colonna, M. TREM-1 amplifies inflammation and is a crucial mediator of septic shock. Nature 410, 1103-1107 (2001).

Bouchon, A., Dietrich, J. & Colonna, M. Cutting edge: inflammatory responses can be triggered by TREM-1, a novel receptor expressed on neutrophils and monocytes. J. Immunol 164, 4991-4995 (2000).

Gibot, S. Clinical review: role of triggering receptor expressed on myeloid cells-1 during sepsis. Crit Care 9, 485-489 (2005).

Gibot, S. et al. Modulation of the triggering receptor expressed on the myeloid cell type 1 pathway in murine septic shock. Infect. Immun 74, 2823-2830 (2006).

Gibot, S. et al. TREM-1 promotes survival during septic shock in mice. Eur. J. Immunol 37, 456-466 (2007).

Hara, H. et al. The adaptor protein CARD9 is essential for the activation of myeloid cells through ITAM-associated and Toll-like receptors. Nat Immunol 8, 619-629 (2007).

Haselmayer, P., Grosse-Hovest, L., von Landenberg, P., Schild, H. & Radsak, M. P. TREM-1 ligand expression on platelets enhances neutrophil activation. Blood 110, 1029-1035 (2007).

Haselmayer, P. et al. Signaling Pathways of the TREM-1- and TLR4-Mediated Neutrophil Oxidative Burst. J Innate Immun 1, 582-591 (2009).

Kelker, M. S., Debler, E. W. & Wilson, I. A. Crystal structure of mouse triggering receptor expressed on myeloid cells 1 (TREM-1) at 1.76 A. J. Mol. Biol 344, 1175-1181 (2004).

Kelker, M. S. et al. Crystal structure of human triggering receptor expressed on myeloid cells 1 (TREM-1) at 1.47 A. J. Mol. Biol 342, 1237-1248 (2004).

Washington, A. V. et al. A TREM family member, TLT-1, is found exclusively in the alpha-granules of megakaryocytes and platelets. Blood 104, 1042-1047 (2004).

Washington A V, Gibot S, Acevedo I, Gattis J, Quigley L, Feltz R, De La Mota A, Schubert R L, Gomez-Rodriguez J, Cheng J, Dutra A, Pak E, Chertov O, Rivera L, Morales J, Lubkowski J, Hunter R, Schwartzberg P L, McVicar D W. TREM-like transcript-1 protects against inflammation-associated hemorrhage by facilitating platelet aggregation in mice and humans. J Clin Invest. 2009 June; 119(6):1489-501.

---

The invention claimed is:

1. A pharmaceutical composition comprising a therapeutically effective amount of at least one polypeptide consisting of 12 to 16 amino acids comprising SEQ ID NO: 9 and at least one pharmaceutically acceptable excipient.

2. The pharmaceutical composition of claim 1, wherein said at least one polypeptide consists of an amino acid sequence as set forth in SEQ ID NO: 9.

3. An isolated polypeptide consisting of 12 to 16 amino acids comprising SEQ ID NO:9.

4. The isolated polypeptide of claim 3, wherein said polypeptide consists of an amino acid sequence as set forth in SEQ ID NO: 9.

5. A pharmaceutical composition comprising a therapeutically effective amount of at least one polypeptide consisting of 6, 7, 8, 9, 10 or 11 amino acids from the amino acid sequence SEQ ID NO: 4, wherein said at least one polypeptide comprises SEQ ID NO: 6.

6. An isolated polypeptide consisting of 6, 7, 8, 9, 10 or 11 amino acids from the amino acid sequence SEQ ID NO: 4, wherein said polypeptide comprises SEQ ID NO: 6.

7. The pharmaceutical composition of claim 5, wherein said polypeptide consists of an amino acid sequence as set forth in SEQ ID NO: 6.

8. The isolated polypeptide of claim 6, wherein said polypeptide consists of an amino acid sequence as set forth in SEQ ID NO: 6.

9. A pharmaceutical composition comprising a therapeutically effective amount of at least one polypeptide consisting of 6, 7, 8, 9, or 11 amino acids from the amino acid sequence SEQ ID NO: 4, wherein said at least one polypeptide comprises SEQ ID NO: 7 or SEQ ID NO: 8.

10. The pharmaceutical composition of claim 9, wherein said polypeptide consists of an amino acid sequence selected from the group consisting of SEQ ID NO: 7 or SEQ ID NO: 8.

11. An isolated polypeptide consisting of 6, 7, 8, 9, or 11 amino acids from the amino acid sequence SEQ ID NO: 4, wherein said polypeptide comprises SEQ ID NO: 7 or SEQ ID NO: 8.

12. The isolated polypeptide of claim 11, wherein said polypeptide consists of an amino acid sequence selected from the group consisting of SEQ ID NO: 7 or SEQ ID NO: 8.

* * * * *

SEQUENCE LISTING

```
<160> NUMBER OF SEQ ID NOS: 9

<210> SEQ ID NO 1
<211> LENGTH: 311
<212> TYPE: PRT
<213> ORGANISM: Homo sapiens

<400> SEQUENCE: 1

Met Gly Leu Thr Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
        115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
            180                 185                 190

Leu Gly Val Cys Gly Arg Phe Leu Ser Ser Arg Val Ser Gly Met Asn
        195                 200                 205

Pro Ser Ser Val Val His His Val Ser Asp Ser Gly Pro Ala Ala Glu
    210                 215                 220

Leu Pro Leu Asp Val Pro His Ile Arg Leu Asp Ser Pro Pro Ser Phe
225                 230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270
```

```
Leu Val Cys Ser Lys Pro Val Thr Tyr Ala Thr Val Ile Phe Pro Gly
            275                 280                 285
Gly Asn Lys Gly Gly Thr Ser Cys Gly Pro Ala Gln Asn Pro Pro
    290                 295                 300
Asn Asn Gln Thr Pro Ser Ser
305                 310

<210> SEQ ID NO 2
<211> LENGTH: 12
<212> TYPE: PRT
<213> ORGANISM: Homo sapiens

<400> SEQUENCE: 2

Ser Ala Val Asp Arg Arg Ala Pro Ala Gly Arg Arg
1               5                   10

<210> SEQ ID NO 3
<211> LENGTH: 14
<212> TYPE: PRT
<213> ORGANISM: Homo sapiens

<400> SEQUENCE: 3

Cys Met Val Asp Gly Ala Arg Gly Pro Gln Ile Leu His Arg
1               5                   10

<210> SEQ ID NO 4
<211> LENGTH: 17
<212> TYPE: PRT
<213> ORGANISM: Homo sapiens

<400> SEQUENCE: 4

Leu Gln Glu Glu Asp Ala Gly Glu Tyr Gly Cys Met Val Asp Gly Ala
1               5                   10                  15
Arg

<210> SEQ ID NO 5
<211> LENGTH: 17
<212> TYPE: PRT
<213> ORGANISM: Homo sapiens

<400> SEQUENCE: 5

Gly Ala Glu Arg Glu Val Cys Met Asp Glu Tyr Gly Ala Leu Gln Asp
1               5                   10                  15
Gly

<210> SEQ ID NO 6
<211> LENGTH: 6
<212> TYPE: PRT
<213> ORGANISM: Homo sapiens

<400> SEQUENCE: 6

Leu Gln Glu Glu Asp Ala
1               5

<210> SEQ ID NO 7
<211> LENGTH: 6
<212> TYPE: PRT
<213> ORGANISM: Homo sapiens

<400> SEQUENCE: 7

Glu Asp Ala Gly Glu Tyr
1               5
```

```
<210> SEQ ID NO 8
<211> LENGTH: 6
<212> TYPE: PRT
<213> ORGANISM: Homo sapiens

<400> SEQUENCE: 8

Gly Glu Tyr Gly Cys Met
1               5

<210> SEQ ID NO 9
<211> LENGTH: 12
<212> TYPE: PRT
<213> ORGANISM: Homo sapiens

<400> SEQUENCE: 9

Leu Gln Glu Glu Asp Ala Gly Glu Tyr Gly Cys Met
1               5                   10
```